United States Patent [19]

Bickelhaupt

[11] Patent Number: 4,858,821
[45] Date of Patent: Aug. 22, 1989

[54] PACKAGE AND LID WITH CONTROLLED TEARING MEANS

[75] Inventor: Roger G. Bickelhaupt, Modjeska Canyon, Calif.

[73] Assignee: Baxter International Inc., Deerfield, Ill.

[21] Appl. No.: 270,320

[22] Filed: Nov. 14, 1988

[51] Int. Cl.[4] .............................................. B65D 77/38
[52] U.S. Cl. ................................. 229/123.1; 206/364; 206/631; 206/633; 229/123.2
[58] Field of Search ....................... 206/364, 631, 633; 229/123.1, 123.2

[56] References Cited

U.S. PATENT DOCUMENTS

| | | | |
|---|---|---|---|
| 2,640,623 | 6/1953 | Ryder | 220/23.4 |
| 2,990,948 | 7/1961 | Zackheim | 206/633 X |
| 3,185,578 | 5/1965 | Scharre | 206/631 X |
| 3,215,333 | 11/1965 | Stelzer | 206/633 X |
| 4,209,126 | 6/1980 | Elias | 229/123.2 |
| 4,366,901 | 1/1983 | Short | 206/364 X |
| 4,673,085 | 6/1987 | Badouard et al. | 206/631 X |

Primary Examiner—Stephen Marcus
Assistant Examiner—Kathyrn M. Stemann
Attorney, Agent, or Firm—Debra E. Dahl

[57] ABSTRACT

A package having a peelable lid with a controlled tearing guide, comprising a bottom tray having an inner surface defining a receptacle for an object to be packaged and a continuous rim extending around the periphery of the tray and projecting into the interior of the tray at least once at a given point on the periphery to define two compartments in the tray joined by a channel; (b) a lid extending over the bottom tray and having a peripheral edge portion continuously overlying the peripheral rim of the bottom tray and having a predetermined tear line overlying the inward projecting portion of the rim; (c) a heat seal coating applied to the interior surface of the lid in contact with the continuous rim of the bottom tray for heat sealing the lid to the bottom tray; and (d) a controlled tearing guide on the lid for guiding the tear line across one compartment of the tray so that the other compartment of the tray is not exposed when the lid is selectively torn open along the predetermined tear line.

13 Claims, 3 Drawing Sheets

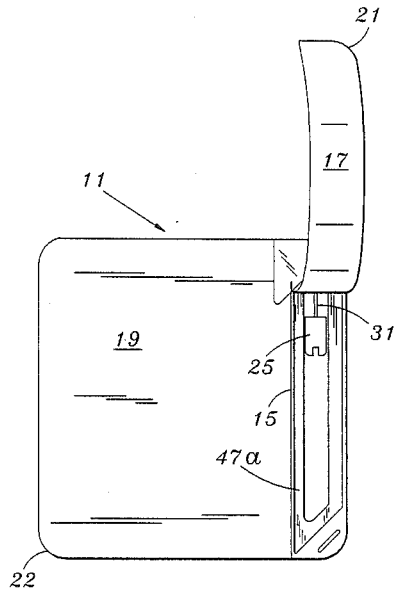

PACKAGE AND LID WITH CONTROLLED TEARING MEANS

FIELD OF INVENTION

In general, the present invention relates to a heat-sealable, sterilizable package having a lid with portions that can be sequentially peeled open. Specifically, the present invention relates to packages for medical devices where it is desirable to peel open a portion of the lid to gain access to the non-invasive portion of the device for prepatory tasks, such as calibration or the like, without contaminating the invasive portion of the device.

BACKGROUND OF THE INVENTION

In the medical field, catheters and other medical devices are commonly packaged in molded plastic trays with various indentations and compartments for holding securely and neatly in place the various parts of the device, such as the coil of a catheter, the connector between the catheter and the extension tubes, and the extension tubes. The package is then heat-sealed with a thin flexible lid having adhesive backing, and sterilized with the device in the package.

The lid is generally made from a polymeric sheet material that provides a breathable, sterile barrier and then coated on one side with a heat sealable coating, usually a hot melt adhesive system. Raised surfaces or rims are formed around the periphery of the tray to provide a surface for heat sealing the lid onto the tray. Tabs are usually formed in the lid so that the lid can be easily grasped and peeled open when the medical device is needed.

There are times when it is desirable to peel or tear open only a portion of the lid to gain access to a portion of the medical device, usually the noninvasive portion, while retaining the sterility of the other portion of the device, usually the invasive portion, that is, the portion that enters the patient's body. Lids have been provided with two tabs, one for peeling open one portion of the lid to expose one compartment of the package and one for peeling open the other portion of the lid to expose the other compartment of the package. In practice, however, the portion of the lid the user intends to peel or tear open sometimes tears over to expose the other compartment, risking contamination of the invasive portion of the device. The shredding that results allows loose particulate matter to enter the compartment, increasing the likelihood of contamination.

Sealable and sterilizable packages with heat sealed, peelable lids have also been used in the food packaging industry. See, for example, U.S. Pat. No. 3,946,871, issued March 30, 1976, in the name of Sturm, for a Sealable and Sterilizable Package. There have been other prior art containers with membrane type closures that can be partially torn open along a defined tear line to form a dispensing opening. See, for example, U.S. Pat. No. 4,209,126, issued June 24, 1980, in the name of Elias, for a Patch Top Closure Member Including a Monoaxially Oriented Film Layer. In Elias, the defined tear line is achieved by providing a lid with at least one layer of mono-axially oriented plastic film having a grain pattern parallel to the desired tear line and providing a tear-initiating cut at the periphery of the lid adjacent the tear-initiating tab. In Elias, there is no attempt to control the direction of the tear line as in the present invention.

There is a need for a package having a peelable lid and means for controlling the direction of tearing open the lid, while providing a clean tear line and reducing the amount of particulate generated by the tear. This need is especially felt in the medical field where it is desirable to peel open only one portion of the lid at a time in order to perform preparatory tasks, such as calibrating the medical device.

It is therefore an object of the present invention to provide a package having a peelable lid and means for controlling the direction of tearing open the lid, while providing a clean tear line and reducing the amount of particulate generated by the tear.

SUMMARY OF THE INVENTION

In general, the present invention provides a package having a peelable lid with controlled tearing means. The package includes a bottom tray having an inner surface defining a receptacle for an object, such as a medical device. The bottom tray has a continuous rim or raised surface extending around the periphery of the tray. The continuous rim projects into the interior of the tray at least once at a given point on the periphery, thereby defining two compartments in the tray joined by a channel. The inwardly projecting portion of the rim can be formed to provide a single rim or can form a looped rim having inward and outward projecting portions with a groove in between.

A flexible, peelable lid extends over the bottom tray and has a peripheral edge portion continuously overlying the peripheral rim or raised surface of the bottom tray. The lid has a predetermined tear line overlying the inwardly projecting portion of the rim, or overlying the groove, if a groove is provided between the inward and outward projecting portions of a looped rim.

Controlled tearing means is provided on the lid for directing the tear line across one compartment of the tray so that only one compartment of the tray is exposed when the lid is selectively peeled or torn open along the predetermined tear line. The lid has a heat-sealable, adhesive coating applied to its interior surface which contacts the continuous rim of the bottom tray for heat sealing the lid to the bottom tray.

Preferably, for medical packaging, the bottom tray is a molded thermoplastic material with indentations corresponding to the various pieces of the medical device. The tray is preferably a clear plastic material, such as acrylonitrile. The lid is a flexible, peelable sheet material, preferably, a polymeric sheet material such as spun bond polyolefin, which provides a breathable sterile barrier and can be coated with a heat-sealable coating, such as a hot melt adhesive system.

Preferably, the controlled tearing means is made of a polymeric sheet material, such as polyester film, that is strong enough to withstand the tearing force of the lid as the lid encounters the controlled tearing means. Otherwise, the edge of the controlled tearing means that directs and guides the tear line could be torn through by the lid. The controlled tearing means is preferably adhesively applied to the exterior of the lid with an adhesive, such as a pressure sensitive, solvent based, permanent adhesive, that has a bonding strength sufficient to withstand the tearing force as the tearing portion of the lid encounters the controlled tearing means.

The controlled tearing means preferably defines a tearing line that cuts diagonally across one compartment of the tray from the termination point of the predetermined tear line. The controlled tearing means is preferably disposed over the channel between the two compartments of the tray so that when a portion of the lid is torn away along the diagonal line defined by the controlled tearing means, the channel is not exposed.

If the package has been sterilized as it would be for medical use, the sterility barrier is technically broken when the first portion of the package is opened. However, because the channel connecting the two compartments is completely covered by the lid, the chances of contaminating the medical device or other object in the closed compartment with bacteria or particulate matter from the tearing lid are substantially reduced, especially in the clean environment of a hospital operating room or intensive care unit.

Depending upon the material used for the lid, the predetermined tear line may need to be precut, perforated or have a tear-initiating cut in order to start the tear. If the lid stock material is easily torn, a tear-initiating cut or slit just at the periphery of the lid may be sufficient to start the tear. The tear-initiating cut at the peripheral edge of the lid is most effective when the lid is made of a mono-axially oriented synthetic material with a grain pattern parallel to the longitudinal axis of the predetermined tear line. If the lid stock material is relatively difficult to tear which would be the case with spun bond polyolefin, a perforated or precut slit may be necessary. The perforated or precut slit would then be heat-sealed to the inward projecting ridge or raised edge to seal the package.

Preferably, the lid is provided with a tab that can be easily grasped to peel or tear open the desired portion of the lid along the predetermined tear line. The tab can be an outward projecting portion of the lid itself which extends beyond the peripheral edge of the bottom tray. Alternatively, the tab can be formed by molding the bottom tray so that the continuous rim cuts across one peripheral corner of the tray rather than around its edge so that when the lid is heat sealed to the continuous rim, one peripheral corner of the lid remains free thereby forming a tab.

The present invention has other objects and features of advantage which will be apparent from and are set forth in more detail in the following detailed description of the invention and the accompanying drawings.

DETAILED DESCRIPTION OF THE INVENTION

Figure 1:
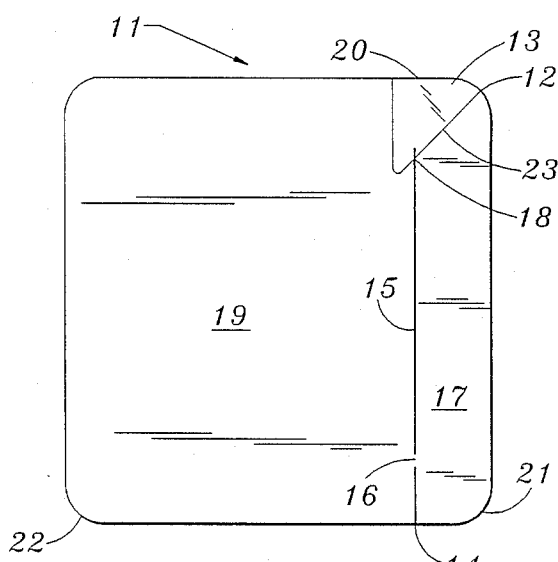
FIG. 1 is a top end view of the package of the present invention with the lid completely closed.

Referring to FIG. 1, there is shown a top end view of the peelable lid 11 of the present invention with controlled tearing means 13 adhesively applied thereto. The predetermined tear line 15 divides the lid into two portions 17 and 19.

While the package and peelable lid of the present invention can be used for packaging a wide variety of objects wherein it is desirable to sequentially open portions of the package, it is particularly advantageous for packaging medical devices. For purposes of illustration, therefore, the present invention will be described as a package for an optical catheter. The package of the present invention is particularly advantageous for packaging an optical catheter because it permits in-package calibration of the optical catheter. One portion of the package can be peeled open to expose only the fiber optic connector, while the remaining portion of the optical catheter, the invasive portion, remains in the closed portion of the package. This minimizes the risk of contamination of the optical catheter during the calibration process.

The lid 11 is made of a flexible, peelable, almost paper-like material that is strong enough to withstand accidental tearing or puncturing during handling or transport of the package. The lid material should provide a breathable sterile barrier that permits sterilization with gaseous ethylene oxide while the device is in the sealed package. Radiation sterilization is an alternative which would not require the lid to be gas permeable or breathable. For medical applications, a preferred material is a polymeric sheet material, such as spun bond polyolefin. Spun bond polyolfin is commercially available for E. I. du Pont Nemours & Company under the trademark Tyvek. Paper can be used because it provides a breathable, sterile barrier but for medical applications is less desirable because it is not as strong as polymeric materials. A metal foil could also be used but is not breathable and would require radiation sterilization.

The lid should be capable of being coated with a heat-sealable coating, such as a commercially available hot melt adhesive system or water based adhesive system, according to known techniques. One preferred hot melt adhesive system is commercially available from Oliver Corporation under the trademark Oliver 18 B.

If the lid stock is made of a material that is not easily torn, such as spun bond polyolefin, it is desirable to form a precut slit along the predetermined tear line 15. The slit can then be heat sealed to the inwardly projecting rim or raised surface of the bottom tray to provide a sterile seal for the package, despite the fact that it is precut. If a precut slit is provided, it is desirable to provide a tab 16 near the beginning of the slit that is not precut to aid in holding the tab 21 in place. Other advantages of the precut slit are reduction in the particulate matter when the first portion of the lid 17 is peeled or torn open, and a clean, straight tear line. A precut slit is a preferred embodiment for the predetermined tear line.

In other embodiments, the tear line 15 can be perforated, or if the lid stock is made of a material that is easily torn along the grain, such as a mono-axially oriented plastic sheet material with a grain running longitudinal to the predetermined tear line, no precut slit or perforation would be required. A tear-initiating cut just at the periphery 14 of the predetermined tear line 15 would of course be preferable to initiate the tear.

The controlled tearing means 13 is preferably adhesively applied to the package lid but could be mechanically applied or attached to the lid, or formed into the lid. The controlled tearing means is preferably applied to the lid between the termination point 18 of the predetermined tear line and the peripheral edge 20 of the lid as shown in FIG. 1. This prevents the tear line from continuing in the same direction across the peripheral edge 20 which is directly opposite the tear-initiating peripheral edge 14. Preferably, the controlled tearing means is shaped to provide a diagonal tear guide 23 as shown in FIG. 1. Preferably, it is triangular shaped with one corner of its base slightly curved to correspond to the curvature of the peripheral corner 12 of the lid.

The controlled tearing means is made from a material that is strong enough to withstand the tearing force of the lid as the lid encounters the guiding edge of the tear guide 23. Thus, the controlled tearing means controls the direction of the tear and is not torn through by the lid. Further, the material of the controlled tearing means must be capable of being adhesively applied to the lid, attached to the lid in some other secure manner, or formed in the lid itself.

A preferred material for the controlled tearing means which has the necessary strength and bonding properties is a polymeric sheet material, such as a polyester film. A preferred polyester is a clear polyester manufactured by E. I. du Pont Nemours & Company under the trademark Mylar. The controlled tearing means could be made of a rigid plastic or a heavy metal foil or any other material which would provide a sharp edge for guiding or directing the tear line but which can be securely fastened or attached to the lid.

In a preferred embodiment, an adhesive coating is applied to one side of the controlled tearing means. The adhesive must have a bonding strength sufficient to withstand the tearing force as the lid is torn and guided by the controlled tearing means. Unlike the adhesive applied to the lid, this adhesive should not be peelable. A preferred adhesive is a solvent based, pressure sensitive, permanent adhesive. The controlled tearing means should be adhesively applied to the lid prior to heat sealing the lid to the bottom tray to further set the adhesive and bind it more securely to the lid.

Preferably, the controlled tearing means is positioned on the lid over the narrow channel between the two compartments in the bottom tray to provide a diagonal tear line 23 across the first portion 17 of the lid so that when the first portion of the lid is torn away, the narrow channel joining the two compartments of the bottom tray is not exposed. This substantially reduces the risk of contaminating the catheter contained in the other compartment of the bottom tray.

Figure 3:
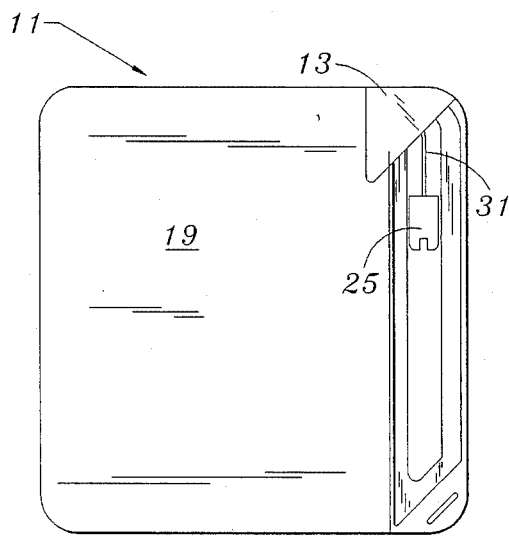
FIG. 3 is a top end view of the package of the present invention with one portion of the lid completely torn off.
Figure 2:
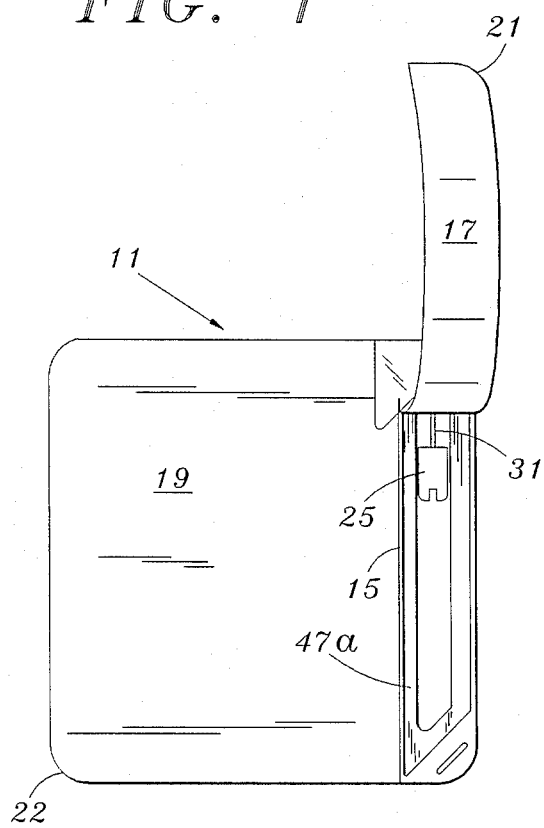
FIG. 2 is a top end view of the package of the present invention with one portion of the lid peeled open.

Referring to FIG. 2, a schematic top plan view of the package of the present invention with portion 17 of the lid peeled open but not torn off is shown. In the partially opened position, fiber optic connector 25 is exposed. When the package of the present invention is used for optical catheters, the physicians are instructed to peel open portion 17 of the lid as shown in FIG. 2 and not to tear it completely off as shown in FIG. 3. This eliminates excess debris and provides for neater packaging.

In practice, however, portion 17 tends to be torn completely off by the physicians as shown in FIG. 3. Thus, the controlled tearing means 13 is needed to ensure that the tearing off of lid portion 17 exposes only the first compartment of the bottom tray to prevent exposure and contamination of the optical catheter or other device contained in the second compartment.

Figure 4:
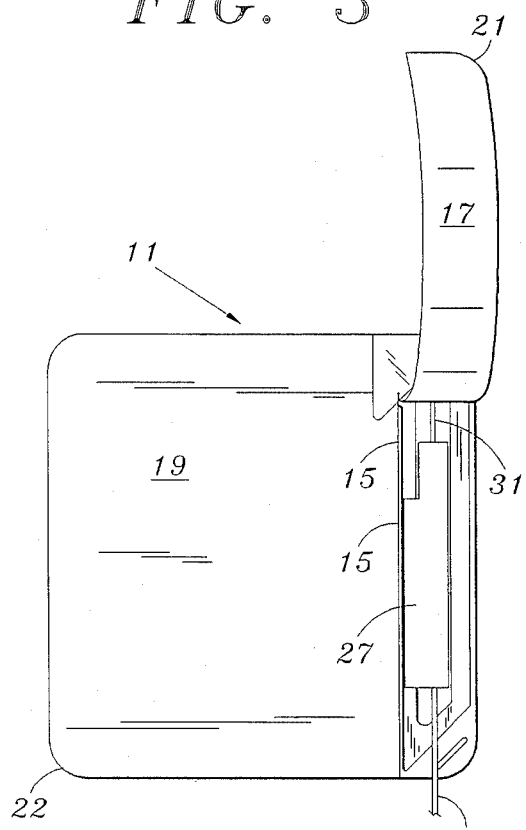
FIG. 4 is a top end view of the package of the present invention with one portion of the lid peeled open to show in-package calibration of an optical catheter.

Referring to FIG. 4, a top end view of the package of the present invention shows lid portion 17 open with fiber optic connector 25 positioned within fiber optic module 27. The fiber optic cable 29 leads from module 27 to an optical instrument (not shown). The instrument transmits light through an optical fiber passing through cable 29, and through module 27 where it connects with an optical fiber in fiber optic connector 25. The light is then transmitted through the optical fiber in fiber optic connector 25 which passes through cable 31, and through one of the lumens of catheter 33 to the distal tip of the catheter.

When the catheter 33 is correctly positioned within a patient's vein, the light from the transmitting optical fiber is directed against the patient's blood. The blood reflects light back to the distal tip of catheter 33 and the light is transmitted through a second optical fiber contained in the same lumen as the transmitting optical fiber and which passes through cable 31 and fiber optic connector 25. It then connects with an optical fiber in module 27 which in turn passes through cable 29 to the instrument. The reflected light forms a signal having a characteristic related to the absorption characteristics of the blood. The light signal is converted to an electrical signal within module 27 and transmitted to the instrument (not shown) for processing in accordance with known techniques to determine the venous oxygen saturation of the blood.

By opening the portion of the package shown in FIG. 3 and FIG. 4, the catheter can be calibrated in the package by attaching module 27 to fiber optic connector 25 and transmitting light from the instrument (not shown) through the transmitting optical fiber in cable 29 through the optical fiber in cable 31 and continuing through the catheter 33 until it reaches the distal opening. In the package, the distal tip of the catheter is contained within a calibration cup 35 shown in FIG. 6. The cup has an opaque cap or shield through which no light is transmitted, thus the light reflected back through the second optical fiber to the instrument establishes a zero point according to known calibration techniques. In-package calibration of an optical catheter without contaminating the invasive portion of the catheter is a significant advantage made possible by the present invention.

Figure 5:
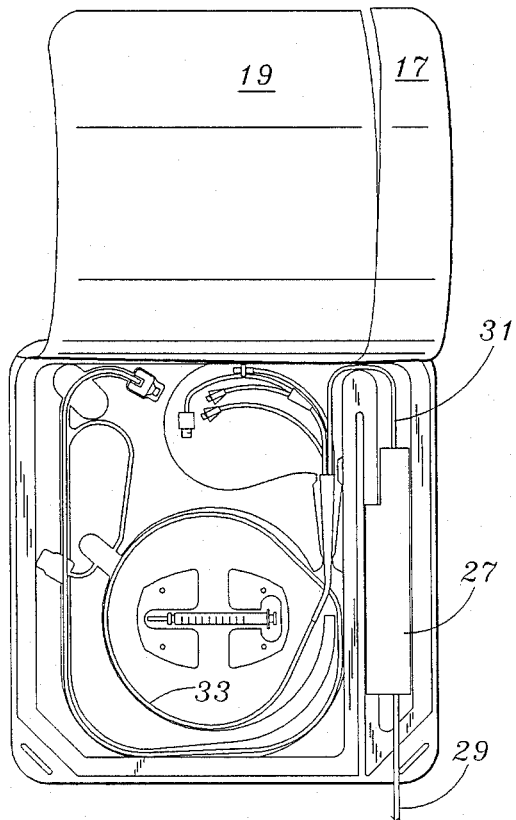
FIG. 5 is a top end view of the package of the present invention with both portions of the lid peeled open to reveal an optical catheter attached to a cable leading to an optical instrument.

Referring to FIG. 5, a top end view of the package of the present invention containing the optical catheter attached to module 27 is shown with both portions of the lid peeled open but not torn off.

Figure 6:
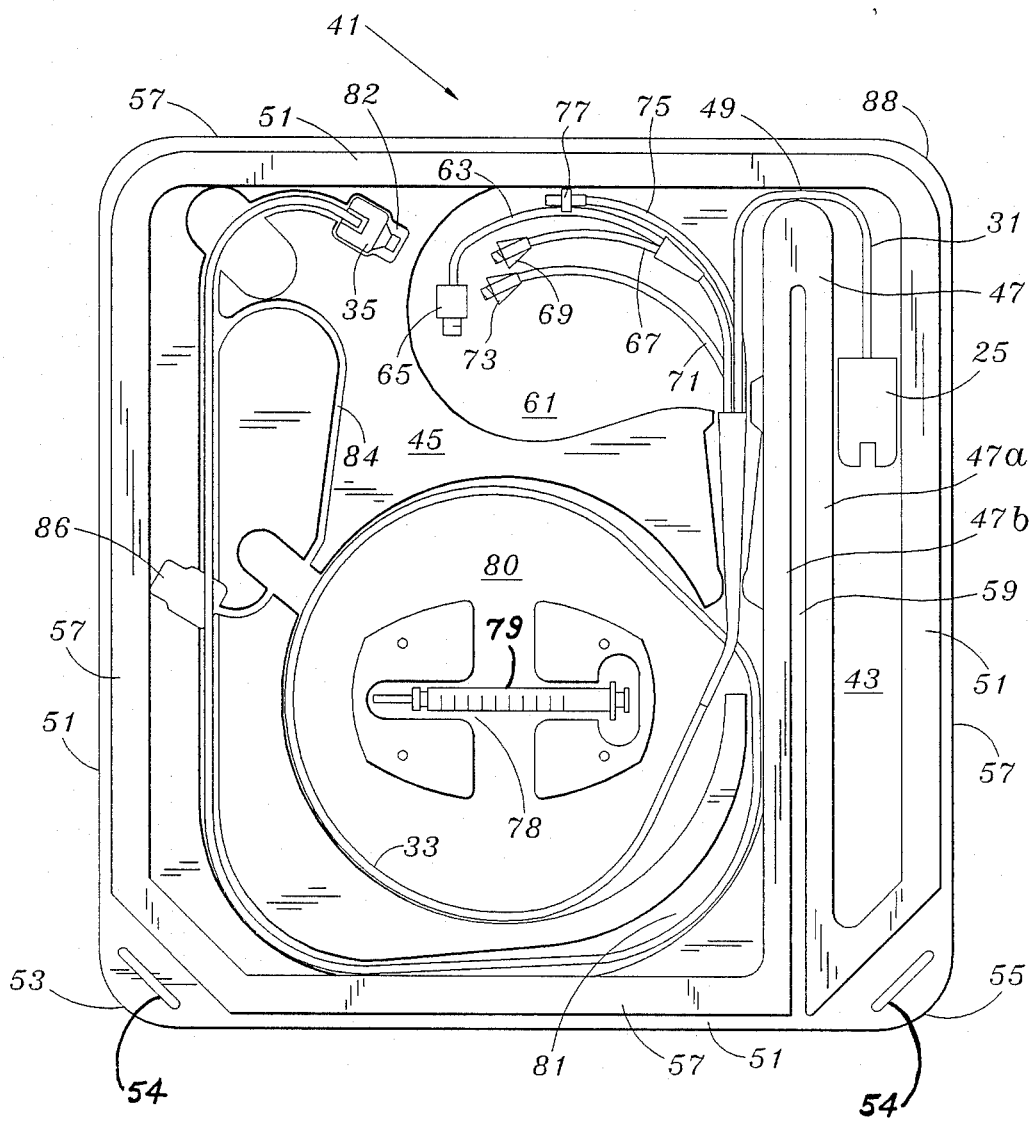
FIG. 6 is a top end view of the bottom tray of the package of the present invention.

Referring to FIG. 6, the bottom tray of the package of the present invention is shown with both portions of the lid peeled or torn off, or prior to having the lid heat sealed in place. The bottom tray 41 has a continuous rim or raised surface 51 extending around the periphery of the tray to provide a heat seal surface for the lid. A portion of the continuous rim projects into the interior of the tray defining two compartments 43 and 45 separated by a narrow channel 49.

The continuous rim cuts across corners 53 and 55. The continuous rim extending around the periphery is separated from the peripheral edge of the bottom tray by a narrow lip 57. By providing the continuous rim or raised edge across corners 53 and 55 rather than around the periphery of corners 53 and 55, non heat-sealed portions of the lid at corners 53 and 55 provide tabs for peeling open portion 17 and portion 19 of the lid, respectively. Raised ridges 54 between the continuous rim and the peripheral corners 53 and 55 permit a portion of tab 21 and tab 22 to be heat sealed to prevent them from flapping loosely or bending when the lid is closed.

In an alternate embodiment, the continuous rim 51 can extend around the periphery of corners 53 and 55, and the lid itself may have tabs formed in it which extend beyond the peripheral edge of the bottom tray.

The inward projecting portion of the rim 47 provides the heat seal surface over which the predetermined tear line lies so that portion 17 of the lid can be peeled or torn open to reveal compartment 43 while compartment 45 remains closed. In a preferred embodiment, the inward projecting portion of the rim extends in and out to form a looped ridge as shown in FIG. 6 with a narrow groove 59 between two parallel inwardly projecting rim portions 47a and 47b. In an alternate embodiment, a single raised surface or rim projects into the interior of the tray (not shown).

The advantage of providing the looped inwardly projecting rim with a groove in between is that the predetermined tear line overlying the groove provides a cleaner tear line. This is because the peripheral edges of both sides of the precut slit or perforated slit are not heat sealed to the rim but lie over the groove. Thus, when the first portion of the lid is peeled or torn open, the lid stock tears cleanly along the predetermined tear line and does not delaminate along the tear line as tends to happen when the tear line itself is heat sealed to the rim.

Another advantage of providing the groove is that there is less chance of interrupting the seal between the inwardly projecting portion of the rim 47b and the closed compartment 45 when the lid is peeled open along the predetermined tear line. This is because each portion of the lid on either side of the pre-cut slit or perforated tear line is separately sealed to rim portions 47a and 47b, respectively.

The triangular-shaped tear controlling means is applied to the lid over the narrow channel 49 between compartments 43 and 45, providing a diagonal tear line across compartment 43 extending from the termination point 18 of the predetermined tear line which coincides with the termination point of the groove 59.

The bottom tray can be made of any commercially available thermoformable material, preferably a thermoplastic material, which is capable of being heat sealed to the heat seal coating of the lid. Preferred thermoplastic materials are polystyrene, polyvinyl chloride, and acrylonitrile. For medical applications, a clear plastic such as acrylonitrile is preferred. Acrylonitrile is commercially available from British Petroleum Corporation under the trademark Barex. The acrylonitrile is extruded into sheets or rolls and then molded into trays having the various indentations and compartments needed to contain the various portions of the product to be packaged.

As shown in FIG. 6, the bottom tray is molded to provide the continuous rim 51 and the inward projecting portion of the rim 47, the recessed compartment 43 for the fiber optic connector 25, the narrow channel 49 for the fiber optic cable 31 containing the optical fibers, and recessed compartment 45 for the optical catheter 33. Within compartment 45 there are several indented receptacles.

Receptacle 61 is circular in shape and contains the extension tubes for the various lumens of the catheter and their connectors. Extension tube 63 connects to the inflation lumen and connector 65 can be attached to an air source for inflating the balloon at the distal tip of the catheter. Extension tube 67 contains the thermistor wires which are fed through the inflation lumen and connector 69 can be attached to a temperature monitor. Extension tube 71 connects to the proximal injectate lumen and connector 73 can be connected to a source of injectate. Extension tube 75 connects to the through lumen and connector 77 can be attached to a pressure monitor for measuring pressure at the distal tip, or can be attached to an infusion source. The syringe 79 contained in receptacle 78 of the tray is used for inflating the balloon. Catheter 33 coils through receptacle 80 of the tray and is fed through channel 81 to the calibration cup 35. Receptacle 82 contains the calibration cup 35. Channel 84 and receptacle 86 are provided for use when longer optical catheters are packaged in the tray.

Figure 7:
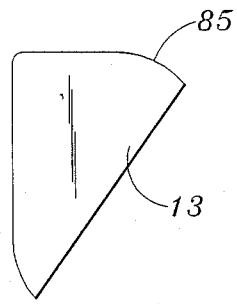
FIG. 7 is a top end view of the controlled tearing means of the present invention.

FIG. 7 shows a preferred shape of the controlled tearing means of the present invention. It is essentially triangular in shape to provide a diagonal tear guide across compartment 43 but has rounded edge 85 so that it lies flush with the rounded corner 12 of the lid which corresponds to the rounded peripheral corner 88 of the bottom tray.

Figure 8:
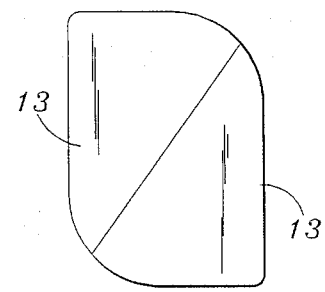
FIG. 8 is a top end view of two controlled tearing means cut from a sheet.
Figure 9:
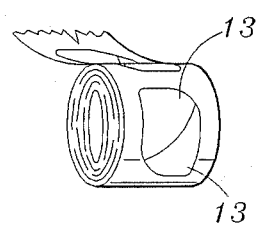
FIG. 9 is a perspective view of a dispenser roll showing how the controlled tearing means can be packaged prior to attachment to the lid.

FIG. 8 shows a pair of controlled tearing means as they appear after being cut from a sheet of the polymeric material. FIG. 9 shows a preferred means of packaging and dispensing the controlled tearing means. A pair of controlled tearing means are cut from a sheet with an adhesive coating on one side that is attached to release paper. The release paper has a shiny smooth surface to which the sheet can be attached without loosing its adhesive properties. The release paper with the precut controlled tearing means is then cut and rolled into a dispenser roll shown in FIG. 9. When ready to be applied to a package lid, a single controlled tearing means can be pulled from the roll shown in FIG. 9 and applied to the lid.

The lid is then placed over the bottom tray, so that the corresponding corners and peripheral edges of the bottom tray and the lid are lined up with each other and the predetermined tear line 15 lies over the inwardly projecting ridge or over the groove, if a looped ridge and groove are provided. The package is then placed in a heat seal fixture where a hot platen presses down on the lid to heat seal the lid to the package according to known techniques.

Depending upon the particular device or object to be packaged, the bottom tray can be formed with variously shaped compartments, receptacles, and channels. The present invention is particularly useful for medical devices, and especially for optical catheters because of the in-package calibration feature, but has many other possible applications both in the medical industry and in other industries. Thus, an exemplary embodiment of the invention has been shown and described but many changes, modifications and substitutions may be made by one having ordinary skill in the art without necessarily departing from the spirit and scope of this invention.

What is claimed is:

1. A package having a peelable lid, comprising:
   (a) a bottom tray having an inner surface defining a receptacle for an object to be packaged and a continuous rim extending around the periphery of the tray, projecting into the interior of the tray at least once at a given point on the periphery, and returning to the periphery of the tray at an adjacent point, defining a groove between an inward projecting portion and an outward projecting portion of the rim, and defining at least two compartments in the tray joined by a channel;

(b) a lid extending over the bottom tray and having a peripheral edge portion continuously overlying the peripheral rim of the bottom tray and having a predetermined tear line overlying said groove;

(c) a heat seal coating applied to the interior surface of the lid in contact with the continuous rim of the bottom tray for heat sealing the lid to the bottom tray; and (d) controlled tearing means on the lid for directing the tear line across one compartment of the tray so that the other compartment of the tray is not exposed when the lid is selectively torn open along the predetermined tear line.

2. A package having a peelable lid, comprising:

(a) a bottom tray having an inner surface defining a receptacle for an object to be packaged and a continuous rim extending around the periphery of the tray and projecting into the interior of the tray at least once at a given point on the periphery to define at least two compartments in the tray joined by a channel;

(b) a lid extending over the bottom tray and having a peripheral edge portion continuously overlying the peripheral rim of the bottom tray and having a predetermined tear line overlying said inward projecting portion of the rim;

(c) a heat seal coating applied to the interior surface of the lid in contact with the continuous rim of the bottom tray for heat sealing the lid to the bottom tray; and (d) controlled tearing means on the lid for guiding the tear line across one compartment of the tray so that the other compartment of the tray is not exposed when the lid is selectively torn open along the predetermined tear line.

3. A package according to claim 1 or 2, wherein said controlled tearing means is adhesively applied to the exterior of the lid with a bonding strength sufficient to withstand the tearing force as a portion of the lid is torn and guided by the controlled tearing means.

4. A package according to claim 1 or 2, wherein said controlled tearing means defines a tearing line that cuts diagonally across one compartment of the tray.

5. A package according to claim 1 or 2, wherein said controlled tearing means is disposed over the channel between the two compartments of the tray so that when a portion of the lid is torn open along the tear line defined by the controlled tearing means, the channel is not exposed.

6. A package according to claim 1 or 2, wherein said controlled tearing means is made of a polymeric sheet material strong enough to withstand the tearing force of the lid so that the edge of the controlled tearing means guides the tear and is not torn by the tearing force of the lid.

7. A package according to claim 6, wherein said controlled tearing means is made of a polyester film with an adhesive backing.

8. A package according to claim 1 or 2, wherein said predetermined tear line is perforated.

9. A package according to claim 1 or 2, wherein said predetermined tear line has a tear-initiating cut at the peripheral edge of the lid and said lid is made of a monoaxially oriented synthetic plastic sheet material, the grain pattern of which extends in a direction parallel with the longitudinal axis of the predetermined tear line.

10. A package according to claim 1 or 2, wherein said predetermined tear line is a precut slit.

11. A package according to claim 10, wherein said predetermined tear line is a precut slit beginning at one peripheral edge of the lid, interrupted by a tab joining the two portions of the lid defined by the slit, and extending to the controlled tearing means.

12. A package according to claim 1 or 2, wherein the lid has a tab that projects outwardly beyond the peripheral edge of the bottom tray so that it can be easily grasped to peel open one portion of the lid.

13. A package according to claim 1 or 2, wherein the continuous rim of the bottom tray cuts across one peripheral corner of the tray such that when the lid is heat sealed to the continuous rim, one peripheral corner of the lid remains free, thereby forming a tab that can be easily grasped to peel open one portion of the lid.

* * * * *